US011433145B2

(12) United States Patent
Kim et al.

(10) Patent No.: US 11,433,145 B2
(45) Date of Patent: Sep. 6, 2022

(54) COMPOSITION FOR TREATING PAIN

(71) Applicant: KOLON LIFE SCIENCE, INC., Gwacheon-si (KR)

(72) Inventors: Sujeong Kim, Seoul (KR); Heonsik Choi, Seoul (KR); Kyoungbaek Choi, Incheon (KR); Minjung Kim, Seoul (KR); Hyeonyoul Lee, Ansan-si (KR); Minju Kim, Seoul (KR); Daewook Kim, Yongin-si (KR); Min Kim, Seoul (KR); Jangjoon Park, Seoul (KR)

(73) Assignee: KOLON LIFE SCIENCE, INC., Gwacheon-si (KR)

( * ) Notice: Subject to any disclaimer, the term of this patent is extended or adjusted under 35 U.S.C. 154(b) by 585 days.

(21) Appl. No.: 15/754,849

(22) PCT Filed: Sep. 20, 2016

(86) PCT No.: PCT/KR2016/010480
§ 371 (c)(1),
(2) Date: Feb. 23, 2018

(87) PCT Pub. No.: WO2017/052160
PCT Pub. Date: Mar. 30, 2017

(65) Prior Publication Data
US 2018/0250421 A1 Sep. 6, 2018

(30) Foreign Application Priority Data
Sep. 21, 2015 (KR) .................. 10-2015-0133349

(51) Int. Cl.
*A61K 48/00* (2006.01)
*C12N 15/63* (2006.01)
*C12N 15/864* (2006.01)
*A61P 25/04* (2006.01)
*A61P 25/28* (2006.01)
*C12N 9/88* (2006.01)
*A61K 38/20* (2006.01)
*A61K 38/43* (2006.01)
*A61K 38/16* (2006.01)
*A61K 9/00* (2006.01)
*A61K 38/17* (2006.01)
*C07K 14/54* (2006.01)
*A61K 47/69* (2017.01)
*A61P 29/00* (2006.01)
*A61K 38/51* (2006.01)

(52) U.S. Cl.
CPC .............. *A61K 48/005* (2013.01); *A61K 9/00* (2013.01); *A61K 38/16* (2013.01); *A61K 38/17* (2013.01); *A61K 38/2066* (2013.01); *A61K 38/51* (2013.01); *A61K 47/6901* (2017.08); *A61K 48/00* (2013.01); *A61K 48/0033* (2013.01); *A61P 29/00* (2018.01); *C07K 14/54* (2013.01); *C12N 9/88* (2013.01); *C12N 15/63* (2013.01)

(58) Field of Classification Search
None
See application file for complete search history.

(56) References Cited

U.S. PATENT DOCUMENTS

| 7,544,669 B2* | 6/2009 | Fontoura ................. A61P 29/00 |
| | | 514/44 R |
| 2009/0010948 A1* | 1/2009 | Huang .................. C12N 15/111 |
| | | 424/184.1 |
| 2013/0115218 A1* | 5/2013 | Reiter .................... C07K 16/40 |
| | | 424/139.1 |

FOREIGN PATENT DOCUMENTS

| EP | 1 621 208 A1 | 2/2006 |
| EP | 2 258 841 A1 | 12/2010 |
| KR | 10-2008-0007968 A | 1/2008 |
| WO | 2008/084115 A2 | 7/2008 |

OTHER PUBLICATIONS

Robert et al., Oral Delivery of Glutamic Acid Decarboxylase (GAD)-65 and IL10 by Lactococcus lactis Reverses Diabetes in Recent-Onset NOD Mice, Diabetes, 2014, pp. 2876-2887.*
EAU-439 *Lactococcus lactis* subsp. cremoris Strain SAGX0037, downloaded May 23, 3030, pp. 1-8.*
Shanks et al, Are animal models predictive for humans?, Philosophy, Ethics, and Humanities in Medicine 2009, pp. 1-20.*
Wu et al., Gene Therapy for the Management of Pain, Anesthesiology 2001; 94:1119-32.*
Huang et al., Development of Viral Vectors for Gene Therapy for Chronic Pain, Pain Research and Treatment, pp. 1-8.*
Thakur et al. Viral vector mediated continuous expression of interleukin-10 in DRG alleviates pain in type 1 diabetic animals, Molecular and Cellular Neuroscience 72 (2016) 46-53.*
Palfi et al, Efficacy of codelivery of dual AAV2/5 vectors in the murine retina and hippocampus, Hum Gene Ther. Aug. 2012;23(8):847-58.*
Hirai et al, Intrathecal AAV Serotype 9-mediated Delivery of shRNA Against TRPV1 Attenuates Thermal Hyperalgesia in a Mouse Model of Peripheral Nerve Injury, Molecular Therapy, 2014, pp. 409-419.*
Jean-Marc G Guedon et al., "Current gene therapy using viral vectors for chronic pain", Molecular Pain, 2015, pp. 1-23, vol. 11, No. 27.

(Continued)

*Primary Examiner* — Maria Marvich
(74) *Attorney, Agent, or Firm* — Sughrue Mion, PLLC

(57) ABSTRACT

The present invention relates to: a composition for alleviating or treating pain, the composition comprising glutamate decarboxylase and a gene coding for an anti-inflammatory cytokine; and a method for alleviating or treating pain by using the composition.

10 Claims, 6 Drawing Sheets
Specification includes a Sequence Listing.

(56) References Cited

OTHER PUBLICATIONS

D Wolfe et al., "A human trial of HSV-mediated gene transfer for the treatment of chronic pain", Gene Therapy, 2009, pp. 455-460, vol. 16.

Darren Wolfe, PhD, et al., "A Clinical Trial of Gene Therapy for Chronic Pain", Pain Medicine, 2009, pp. 1325-1330, vol. 10, No. 7.

Erin D. Milligan et al., "Controlling pathological pain by adenovirally driven spinal production of the anti-inflammatory cytokine, interleukin-10", European Journal of Neuroscience, vol. 21, pp. 2136-2148, 2005, 13 pages total.

Jean-Philippe Vit et al., "Adenovector GAD65 gene delivery into the rat trigeminal ganglion produces orofacial analgesia", Molecular Pain, vol. 5, No. 1, Aug. 2009, 11 pages total.

Béla Dénes et al., "Suppression of Hyperglycemia in NOD Mice After Inoculation With Recombinant Vaccinia Viruses", Molecular Biotechnology, vol. 34, No. 3, Nov. 2006, pp. 317-327, 11 pages total.

Sofie Robert et al., "Oral Delivery of Glutamic Acid Decarboxylase (GAD)-65 and IL10 by Lactococcus lactis Reverses Diabetes in Recent-Onset NOD Mice", Diabetes, vol. 63, Aug. 2014, pp. 2876-2887, 12 pages total.

Denes, B. et al., "Durable Multicomponent Vaccine Suppression of Diabetes Autoimmunity", Molecular Therapy, 2009, vol. 17, Supplement 1, p. S67, Abstract 170, 1 page.

Weiss, K. et al., "Herpes simplex virus-based gene therapies for chronic pain", Journal of Pain and Palliative Care Pharmacotherapy, 2012, vol. 26, No. 3, pp. 291-293, 4 pages.

Srinivasan, R. et al.,"HSV vectors for gene therapy of chronic pain", Current Opinion in Molecular Therapeutics, 2008, vol. 10, No. 5, pp. 449-455, 7 pages.

Dénes B. et al., "Autoantigens Plus Interleukin-10 Suppress Diabetes Autoimmunity," Diabetes Technology & Therapeutics, Aug. 2010, vol. 12, No. 8, pp. 649-661 (19 pages).

Milligan et al., "Repeated intrathecal injections of plasmid DNA encoding interleukin-10 produce prolonged reversal of neuropathic pain", PAIN, 2006, vol. 126, pp. 294-308 (total 15 pages).

Kanao et al., "Gene Transfer of Glutamic Acid Decarboxylase 67 by Herpes Simplex Virus Vectors Suppresses Neuropathic Pain Induced by Human Immunodeficiency Virus gp120 Combined with ddC in Rats", Anesthesia & Analgesia, Jun. 2015, vol. 120, No. 6, pp. 1394-1404 (total 11 pages).

Liu et al., "Release of GABA from sensory neurons transduced with a GAD67-expressing vector occurs by non-vesicular mechanisms", Brain Research, 2005, pp. 297-304 (total 8 pages).

Kim et al., "AAV-GAS gene for rat models of neuropathic pain and Parkinson's disease", Acta Neurochirurgica, Supplement, vol. 101, 2008, pp. 99-105 (7 pages total).

Song et al., "Construction and identification of eukaryotic expression vector containing GAD65 fragment and IL-10 gene", Chin Med Biotechnol, 2007, vol. 2, No. 2, pp. 105-109 (5 pages total).

\* cited by examiner

[Fig. 1]
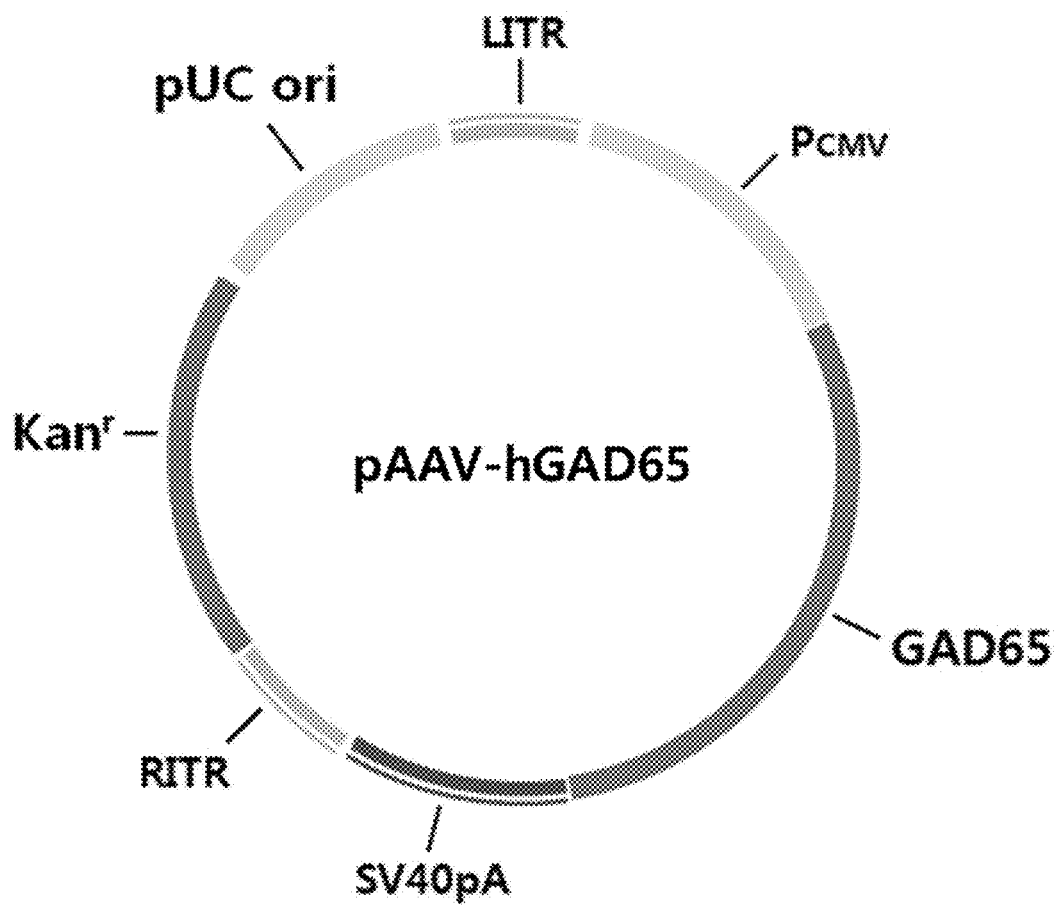

[Fig. 2]
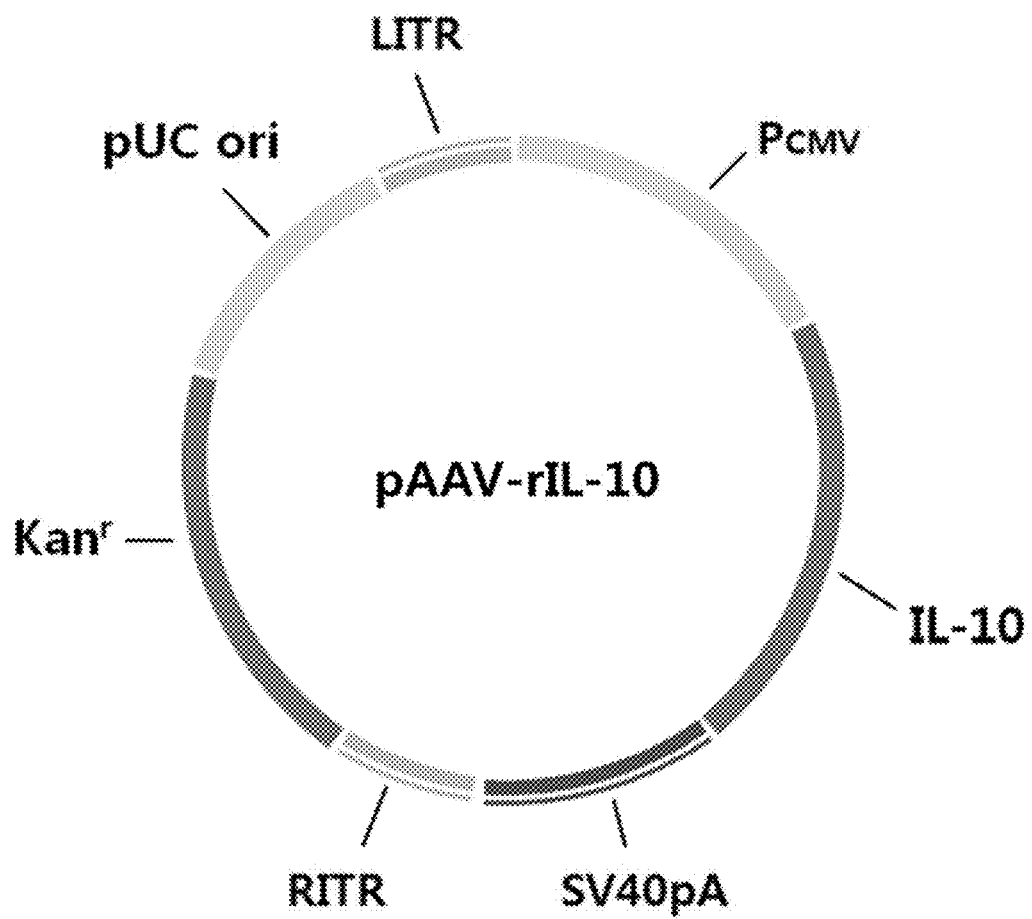

[Fig. 3]
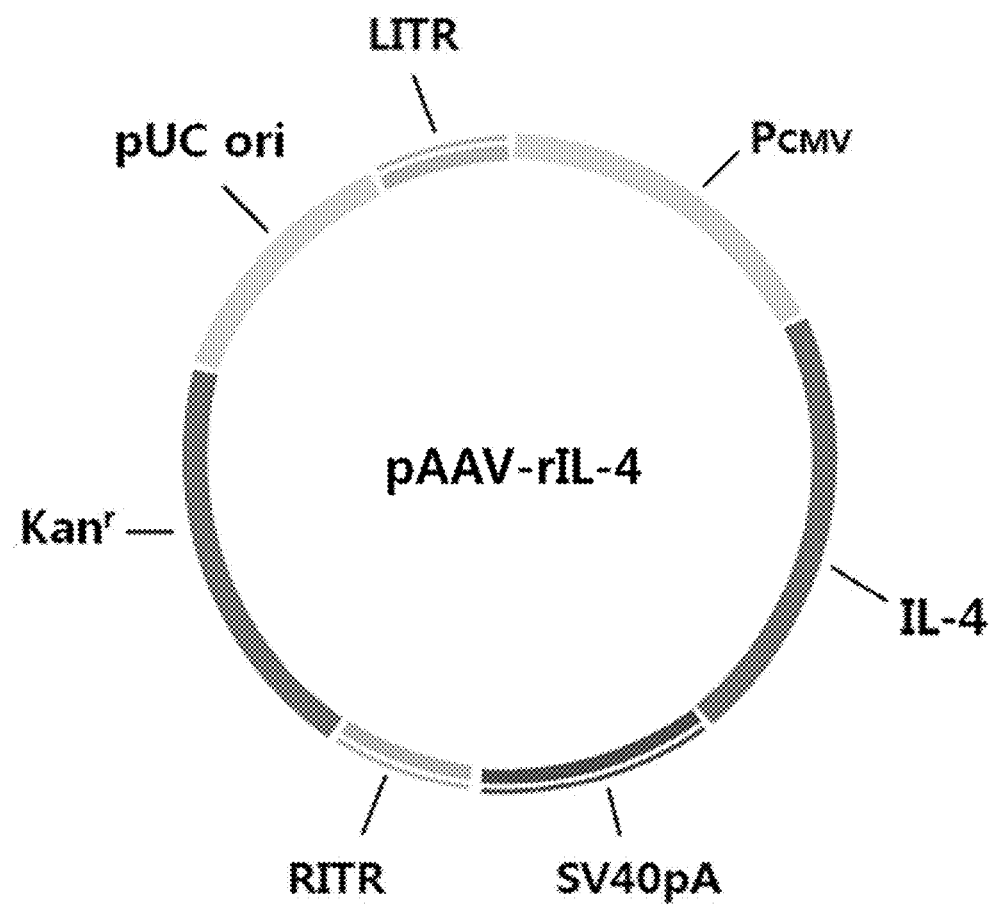

[Fig. 4]
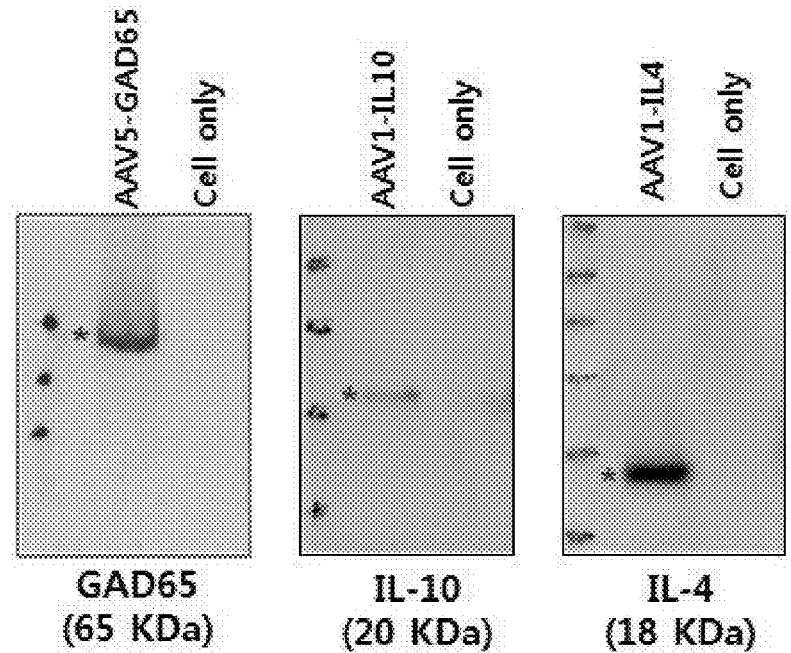
[Fig. 5]
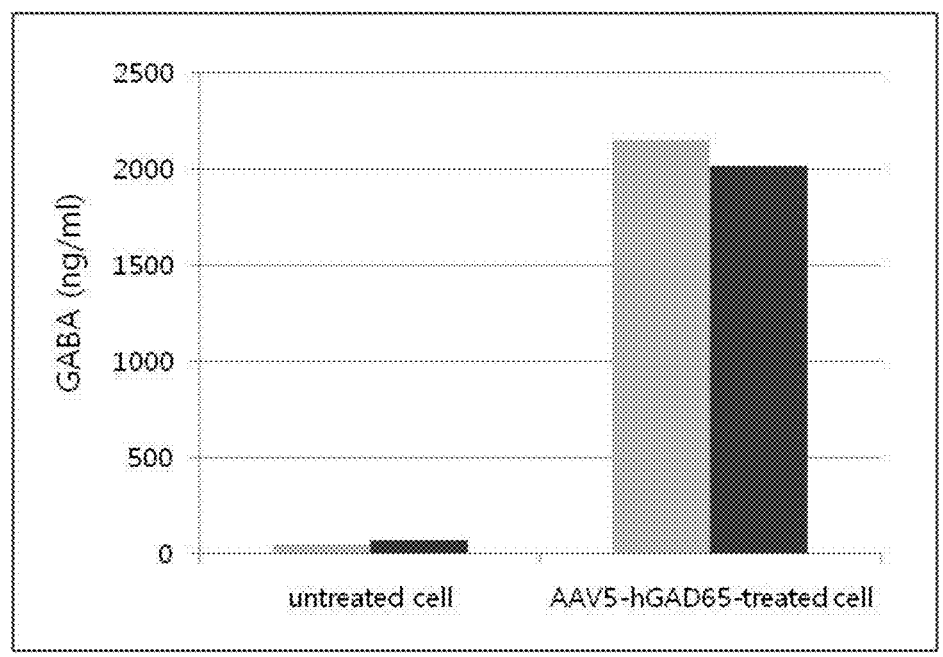

[Fig. 6]
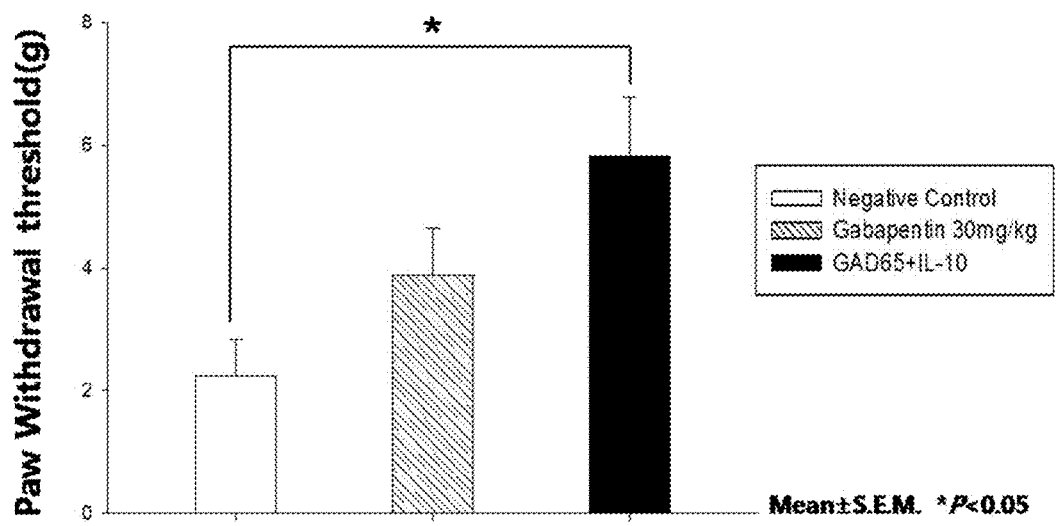
[Fig. 7]
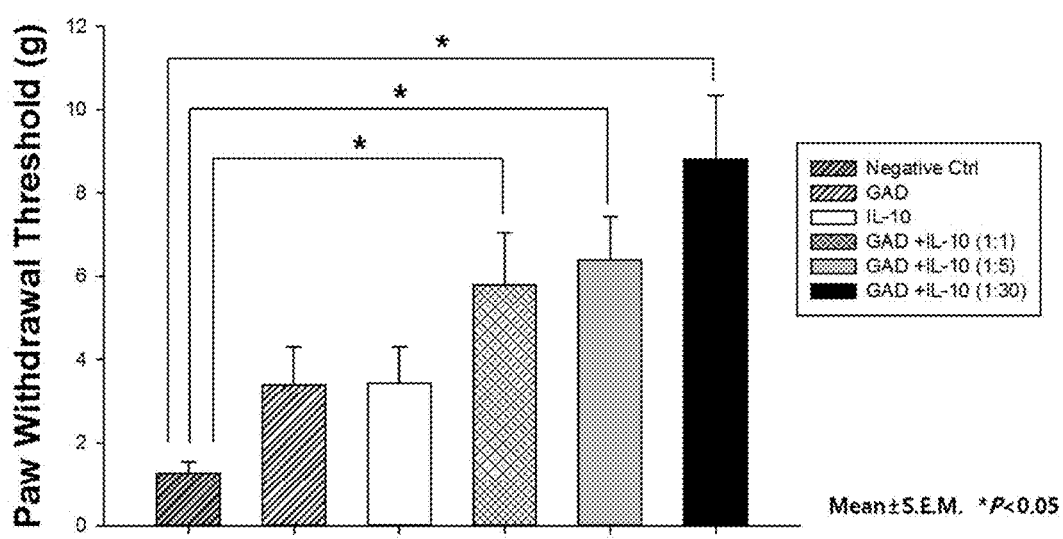

[Fig. 8]
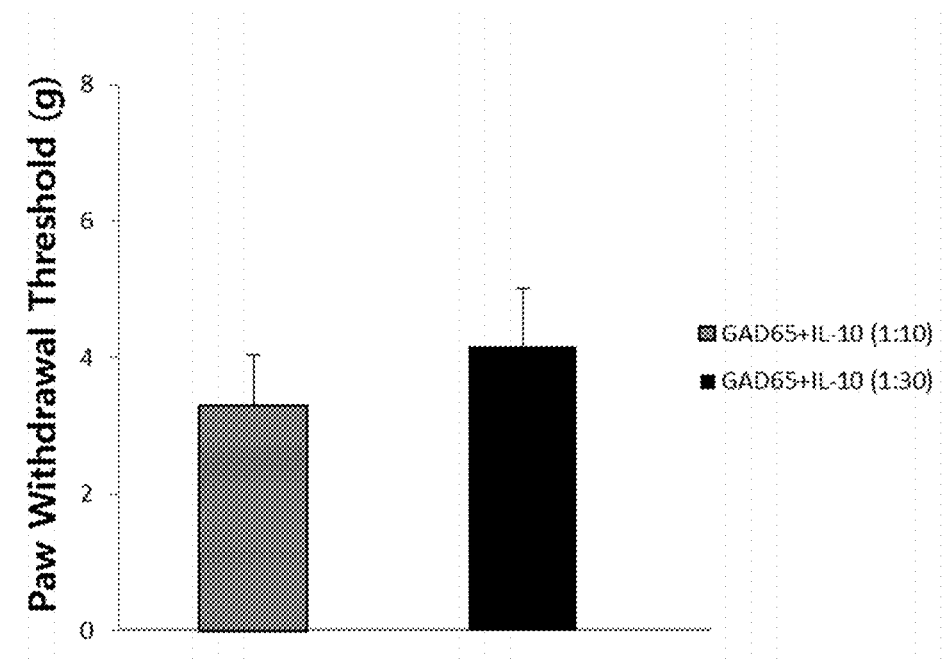
[Fig. 9]
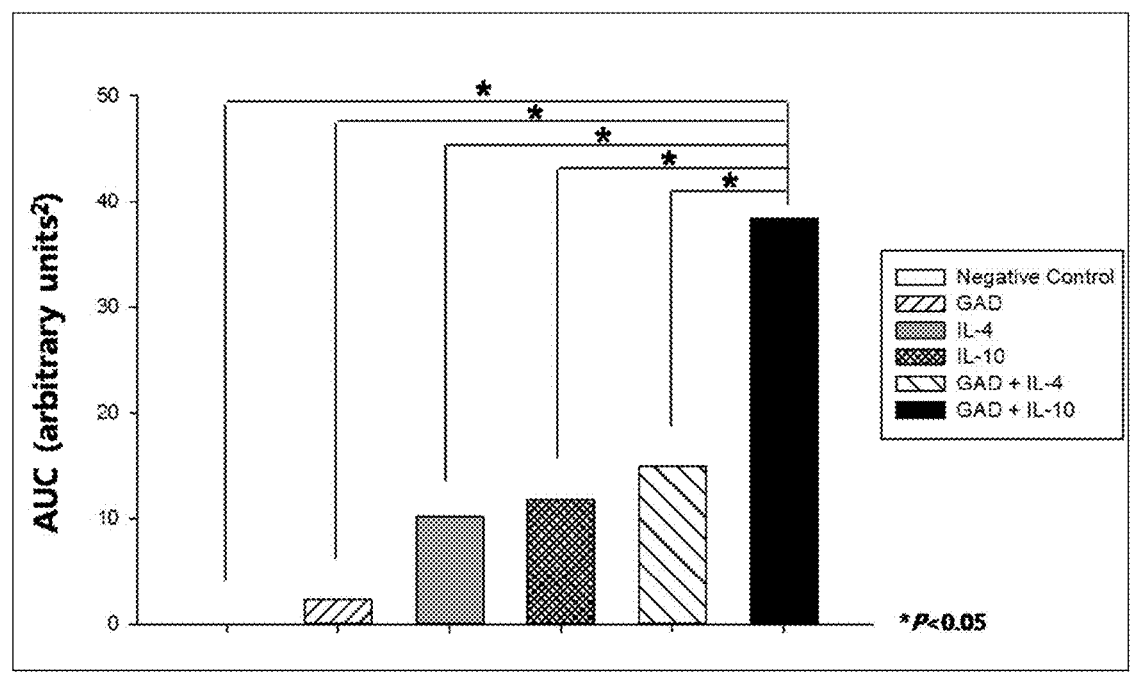

COMPOSITION FOR TREATING PAIN

CROSS REFERENCE TO RELATED APPLICATIONS

This application is a National Stage of International Application No. PCT/KR2016/010480 filed Sep. 20, 2016, claiming priority based on Korean Patent Application No. 10-2015-0133349 filed Sep. 21, 2015.

TECHNICAL FIELD

The present invention relates to a composition for relieving or treating pain, the composition comprising a gene encoding glutamate decarboxylase and a gene encoding an anti-inflammatory cytokine; and a method for relieving or treating pain by using the composition.

BACKGROUND ART

The term "pain" used by the International Association for the Study of Pain is defined as "actual or potential tissue damage or an unpleasant sensory and emotional experience associated therewith." Pain protects parts of the damaged body during the healing of the damage from the damage occurrence and motivates a human being to avoid similar experiences in the future. Most pain is relieved gradually if the cause of stimulus is removed, but sometimes the pain persists even though the damaged site has clearly healed as the stimulus has disappeared, or the pain develops in a state where no irritation, damage or disease has occurred.

Neuropathic pain is a type of non-malignant chronic pain that is induced by abnormality of a nerve, a spinal cord or a brain and is assumed that 1% or more of the population is suffering therefrom. The most common causes of neuropathic pain are trauma, metabolic and ischemic disorders, etc., which cause pathological nerve impulses to be transmitted to the brain through the spinal cord, resulting in pain occurrence. Neuropathic pain can be classified into peripheral neuropathic pain and central neuropathic pain depending on the location affected.

If such neuropathic pain persists for a long period of time, it may lead to mental pain as well as physical pain, and thus, the life quality of a patient is likely to decline. Therefore, active treatment for pain relief should be carried out. Currently, as the pain itself is recognized as a disease and interests in pain is spreading, demand for analgesics is expected to increase steadily in the future. Mainly, analgesics such as acetylsalicylic acid, ibuprofen, and acetaminophen are widely used in current pain treatments. If aspirin, whose main ingredient is acetylsalicylic acid, is used for analgesic purposes, a high dose of at least 500 mg should be administered. However, since aspirin is a non-steroidal anti-inflammatory analgesic (NSAIDs) and interferes with the production of gastric mucosa by blocking the enzyme (COX-1) that promotes the production of prostaglandin which plays a role in protecting gastric mucosa, the stomach can be easily damaged by gastric acid and gastrointestinal bleeding can easily occur. Further, since aspirin prevents thrombus formation, it can cause bleeding. Ibuprofen is also a non-steroidal anti-inflammatory analgesic ingredient, and therefore, it can cause gastric disturbances as well. In case of analgesics whose main ingredient is acetaminophen such as Tylenol, since acetaminophen is metabolized mostly in the liver, the liver may be damaged. Therefore, there are safety issues to lower its maximum dose, etc. In addition, long-term use of the above-mentioned analgesics often lead to resistance and loss of efficacies even if they are efficacious in the early stage, and specifically in case of neuropathic pain, there is a problem that the nonsteroidal anti-inflammatory agent is not effective even in the maximum dose for each patient, and thus high-dose administration for short term is prescribed. Therefore, the development of a new analgesic for neuropathic pain which exhibits excellent analgesic efficacy at low dose without side effects is urgently required.

Currently, several new substances are being developed as analgesics for neuropathic pain. Recently, sodium channel blockers has been developed, but they are mostly in the form of small molecules and have low selectivity to certain isoforms. Further, they show side effects such as cardiotoxicity, motor impairment, etc., and thus, more research in the future is necessary. As for a gene therapeutic agent, Periphagen Holdings Inc. has developed a therapeutic agent in which a gene encoding enkephalin, an opioid peptide, was introduced into herpes simplex virus (HSV) gene carrier. However, in a clinical trial, the problem of declining in its analgesic efficacy has been found, and thus, its progression was halted at phase 2 study. HSV had the advantage of delivering genes to peripheral nerves even when subcutaneously administered, but, in fact, gene delivery efficiency is inferior and it seems to have difficulty in suppressing pain with only enkephalin, an opioid peptide.

DISCLOSURE OF INVENTION

Technical Problem

An example of the present invention relates to a composition for relieving or treating pain, which comprises a gene encoding glutamate decarboxylase (GAD) and a gene encoding an anti-inflammatory cytokine.

An additional example of the present invention is to provide a method for relieving or treating pain comprising administering a gene encoding GAD and a gene encoding an anti-inflammatory cytokine to a subject in need thereof.

Solution to Problem

The present invention provides a pharmaceutical composition for relieving or treating pain, which comprises a gene encoding glutamate decarboxylase (GAD) and a gene encoding an anti-inflammatory cytokine, and a method for relieving or treating pain comprising administering the same to a subject in need thereof.

Advantageous Effects of Invention

A pharmaceutical composition of the present invention can exhibit analgesic effect with only a small amount of gene delivery, and the pain-relieving efficacy can be observed even with a smaller amount of gene delivery as compared to single administration. GABA, a product of the GAD gene, has the efficacy of blocking pain signal transduction, but excessive amount of it can cause symptoms such as itching, dizziness, drowsiness, etc., as well as side effects such as increased heartbeat rate or respiration rate. IL-10 is known to be a cytokine that exhibits anti-inflammatory effect, but side effects such as reducing RBC level, etc., were observed when high dose was used systemically. On the other hand, a pharmaceutical composition of the present invention exhibits excellent analgesic efficacy even with a smaller dose by employing co-administration the combination of GAD and IL-10 as compared to single administration, and thus, it shows the synergistic efficacy of lowering conventional side effects and toxicity by low dose administration.

BRIEF DESCRIPTION OF DRAWINGS

FIG. 1 shows a vector map of the plasmid pAAV-hGAD65 used for the production of recombinant adeno-associated viruses.

FIG. 2 shows a vector map of the plasmid pAAV-rIL-10 used for the production of recombinant adeno-associated viruses.

FIG. 3 shows a vector map of the plasmid pAAV-rIL-4 used for the production of recombinant adeno-associated viruses.

FIG. 4 is a diagram confirming the expression level of each protein by Western blot, where adeno-associated viruses respectively introduced with GAD65, IL-10 and IL-4 genes were prepared, and then 293T cells, a human embryonic kidney cell line, were treated with the viruses, and cells or culture media were collected after 48 hours.

FIG. 5 illustrates the expression of GABA by a recombinant adeno-associated virus AAV-hGAD65, which is a diagram showing GABA levels in the media measured by ELISA, where 293T cells, a human embryonic kidney cell line, were treated with AAB-GAD65, and the culture media were collected after 48 hours. Two identical samples were prepared separately for each experiment group, and the bar represents the value for each sample.

FIG. 6 shows the results of comparing the efficacies of co-administration of AAV-GAD65 and AAV-IL-10 with gabapentin administration, which is a graph confirming the difference in synergistic efficacies of co-administration of AAV-GAD65 and AAV-IL-10 as compared to gabapentin used as a neuropathic pain reliever in the market.

FIG. 7 illustrates efficacies of AAV-GAD65 and AAV-IL-10 depending on combination composition ratios thereof. Particularly, it is a graph showing the synergistic effects in animal behavior analysis with the combination composition ratios of AAV-IL-10 to AAV-GAD of 1:1, 1:5, 1:30.

FIG. 8 is a graph showing the synergistic effects when AAV-GAD65 and AAV-IL-10 were co-administered at 1:10 and 1:30 by transforaminal epidural injection.

FIG. 9 shows the results of comparing the efficacies of AAV-GAD65 and AAV-IL-10 with AAV-GAD65 and AAV-IL-4, which illustrates the synergistic effects in animal behavior analysis when IL-10 and IL-4 were respectively combined with GAD65 for use.

BEST MODE FOR CARRYING OUT THE INVENTION

Hereinafter, the present invention will be described in detail.

In one example of the present invention, a gene encoding GAD and a gene encoding an anti-inflammatory cytokine are provided in a form of being contained in a carrier, and the carrier includes viral vectors and non-viral vectors such as a plasmid, liposome, or the like.

The gene encoding GAD may be operably contained in a first vector, and the gene encoding an anti-inflammatory cytokine may be operably contained in a second vector.

The viral vector may be at least one selected from the group consisting of adenovirus, adeno-associated virus, herpes simplex virus, lentivirus, retrovirus and poxvirus.

A carrier containing a gene encoding GAD according to the present invention (e.g., a first vector) and a carrier containing a gene encoding an anti-inflammatory cytokine (e.g., a second vector) may have a virus titer-based mixing ratio per unit volume of 1:1 to 1:100, 1:1 to 1:80, 1:1 to 1:60, 1:1 to 1:40, 1:1 to 1:20, 1:1 to 1:10, 1:3 to 1:100, 1:3 to 1:80, 1:3 to 1:60, 1:3 to 1:40, 1:3 to 1:20, or 1:3 to 1:10, more preferably 1:1 to 1:50, and most preferably 1:5 to 1:30.

A pharmaceutical composition of the present invention can exhibit analgesic effect with only a small amount of genes or carriers containing the same. The composition of the present invention consists of a vector containing a gene encoding GAD and a vector containing an anti-inflammatory action gene in neural tissues, and the pain-relieving or treating efficacy can be achieved with a smaller amount as compared to single administration by co-administering substances having different analgesic mechanisms. Accordingly, since a composition of the present invention uses a small amount of genes or carriers containing the same, synergy of superior analgesic efficacies is shown while lowering toxicity.

According to an example of the present invention, the first vector and the second vector may be adeno-associated viruses. The adeno-associated virus is not limited to a specific serotype, and preferably, it may be any one of AAV1 to AAV5.

GAD according to the present invention is an enzyme which decarboxylates glutamate to produce GABA (gamma-aminobutyric acid). The gene encoding GAD applicable to the present invention may be one of GAD65 and GAD67, which are two isoforms. The GAD65 may be a human or rat protein or a gene encoding the same, and specific example thereof may consist of the amino acid sequence of SEQ ID NO: 1 of NCBI accession no. NM_000818, and also may consist of the base sequence of SEQ ID NO: 2 or SEQ ID NO: 3. The GAD67 may be a human or rat protein or a gene encoding the same, and specific example thereof may consist of the amino acid sequence of SEQ ID NO: 4 of NCBI accession no. NM_000817, and also may consist of the base sequence of SEQ ID NO: 5.

In a pharmaceutical composition according to the present invention, the inflammatory cytokine may be interleukin-10 (IL-10), and synergistic pain-relieving efficacy is exhibited by co-administration of IL-10 and GAD65.

The IL-10 is one of anti-inflammatory cytokines and is also known as a cytokine synthesis inhibitory factor (CSIF). IL-10 belongs to the class II cytokine and is a homodimer consisting of two subunits of 178 amino acids in length. IL-10 serves the function of inhibiting the activity of NK (natural killer) cells in an immune response, and is involved in signal transduction by forming a complex with the IL-10 receptor. IL-10 may be a human or rat protein or a gene encoding the same, and specific example thereof may consist of the amino acid sequence of SEQ ID NO: 6 of NCBI accession no. NM_012854 or SEQ ID NO: 9 of NCBI accession no. NM_000572, and also may consist of the base sequence of SEQ ID NO: 7, SEQ ID NO: 8 or SEQ ID NO: 10.

The base sequences of the gene encoding GAD and/or the gene encoding IL-10 of the present invention include mutants thereof, which may be base sequences modified by codon optimization for rats or humans. Specifically, the base sequences having sequence homology of at least 60%, preferably 70% or more, more preferably 80% or more, even more preferably 90% or more, most preferably 95% or more are included, where the "sequence homology %" is identified by comparing two optimally arranged sequences and comparison regions, and a part of the sequences in the comparison region may include addition or deletion (i.e., gap) as compared to a reference sequence (not including addition or deletion) regarding the optimal arrangements of the two sequences.

The present invention also provides a method for relieving and/or treating pain comprising administering a therapeutically effective amount of the pharmaceutical composition to a patient in need of relieving and/or treating pain. The above method may further comprise, prior to the administering step, determining the patient as a patient in need of relieving and/or treating pain. The term "therapeutically effective amount" may depend on the amount of an active gradient to achieve a desired efficacy, pain relief and/or therapeutic efficacy.

The pain according to the present invention may include nociceptive pain, psychogenic pain, inflammatory pain associated with tissue damage and immune cell infiltration, pathological pain which is a disease state induced by damage to the nervous system or its abnormal function (dysfunctional pain such as fibromyalgia, irritable bowel syndrome, tension headache), etc. Also, the pain may include back pain distinguished anatomically, such as: neck pain, middle back pain, lower back pain, or tailbone pain. In addition, the pain may include pain such as neuropathic pain, migraine, etc. Neuropathic pain can result from damage or diseases that affect the somatosensory system. Neuropathic pain may be associated with an abnormal sensation called dysesthesia, and with allodynia in which pain sensation is evoked even with painless stimulation. Also, the neuropathic pain may also be a continuous and/or intermittent (seizure) factor. The latter is linked to electric shock in the figurative sense. General characteristics include being hot or cold, pins and needles, numbness, and itching.

In contrast, nociceptive pain is often expressed as "ache". In addition, migraine is a chronic disorder that is associated with a number of autonomic nervous system symptoms and causes headaches of ordinary to severe intensities. The precise mechanisms of these migraines have not been clarified yet. The basic theory is related to the increased excitability of the cerebral cortex and the abnormal regulation of pain nerve cells in the trigeminal nucleus of the brainstem.

As a specific example, pain may be at least one selected from the group consisting of neuropathic pain, cancer pain, postoperative pain, trigeminal neuralgia, idiopathic pain, diabetic neuropathic pain, migraine, etc. As another specific example, the pain may not be a muscle spasm associated with lumbago.

Preferably, a composition of the present invention may be used for relieving or treating neuropathic pain or chronic cancer pain. The term "relieving or treating" refers to any action that alleviates or improves pain symptom by administering a composition of the present invention.

An additional example of the present invention relates to a method for relieving or treating pain comprising administering a gene encoding GAD and a gene encoding an anti-inflammatory cytokine to a subject in need thereof. The subject may be a mammal including a human, or a cell and/or tissue isolated from a mammal including a human. Also, the subject may be a non-human animal, and the term "non-human animal" includes vertebrates such as mammals and non-mammals, for example, primates except humans, sheep, dogs, cats, horses, cows, chickens, amphibians, reptiles, etc.

The therapeutically effective amount and administration route of a pharmaceutical composition of the present invention can be appropriately adjusted in consideration of a condition of the patient, a desired efficacy, and the like by those of ordinary skill in the art. For example, a composition according to the present invention may be provided in the form of an injection, and may include, for example, nerve injection, subcutaneous injection, intramuscular injection, or gene gun injection.

Mode for the Invention

Hereinafter, the present invention is explained in detail by Examples, but the following Examples are intended to further illustrate the present invention without limiting its scope.

Example 1

Preparation and Property Analysis of Recombinant Adeno-Associated Viruses

The adeno-associated viruses required for the present invention were prepared and produced based on the AAV helper-free system (Agilent, USA).

A. Preparation of pAAV-hGAD65

To prepare pAAV-hGAD65 of FIG. 1, the CMV promoter region of pJDK-rGAD65 [Lee B et al., Gene Ther, 12: 1215-1222 (2005)] was amplified by PCR and then introduced into pGEM-T (Promega, USA), to prepare pGEM-T-CMV. The primer sequences used for the amplification of CMV promoter are as follows.

```
F-JDK (SEQ ID NO: 16):
5'-TTCGGCCGTCGAGGAGCTTGGCCCATTG-3'

R-JDK (SEQ ID NO: 17):
5'-GACGTCGACCTAGCTAGCGAATTCGGGGCCGCGGAG-3'
```

The GAD65 gene was prepared by codon-optimization to fit for humans based on the human GAD65 sequence having the amino acid sequence of SEQ ID NO: 1 (NCBI NM_000818) and synthesizing the base sequence of SEQ ID NO: 3 (Bioneer, Korea). The hGAD65 gene introduced into pGEM-T was treated with NheI and SalI to obtain a 1.7 Kb DNA fragment, which was ligated to a 3.7 Kb DNA fragment obtained by treating pGEM-T-CMV with NheI and SalI, to complete pGEM-T-CMV-hGAD65.

SV40pA was amplified by performing PCR using pCI (Invitrogen, USA) as a template, followed by treatment with ClaI and SalI, to obtain a 222 bp DNA fragment. The above fragment was ligated to a 5.4 Kb DNA fragment prepared by cutting pGEM-T-CMV-hGAD65 with ClaI and SalI, to finally prepare pGEM-T-CMV-hGAD65-SV40pA. The primer sequences used for the amplification of SV40pA are as follows.

```
F-SV40pA (SEQ ID NO: 18):
5'-CCATCGATCAGACATGATAAGATACATTGATGAG-3'

R-SV40pA (SEQ ID NO: 19):
5'-GACGTCGACGCGGCCGCTACCACATTTGTAGAGGTTTTACTTG-3'
```

The ampicillin-resistance gene in pAAV-MCS (Agilent, USA) was replaced with kanamycin-resistance gene for the preparation of adeno-associated virus vectors. The kanamycin-resistance gene was amplified by PCR using pET-28(a) (Novagen, USA) as a template, and the amplified 816 bp kanamycin-resistance gene was ligated to pGEM-T, to prepare pGEM-T-Kan$^r$. The primer sequences used for the amplification of kanamycin-resistance gene are as follows.

```
F-Kan (SEQ ID NO: 20):
5'-AGGCGCCATGAGCCATATTCAACGGGAA-3'

R-Kan (SEQ ID NO: 21):
5'-TTCATGATTAGAAAAACTCATCGAGCATC-3'
```

For the introduction of the kanamycin-resistance gene, SpeI and EcoRV sites were respectively generated at the front and back of the ampicillin-resistance gene in pAAV-MCS by mutagenesis, and treated with SpeI and EcoRV, which was then ligated to the DNA fragment obtained by cutting the pGEM-T-Kan$^r$ prepared above with NheI and EcoRV, to prepare pAAV-MCS-Kan$^r$.

The prepared pAAV-MCS-Kan$^r$ was treated with NotI and BamHI, which was then ligated to a 2.7 Kb DNA fragment obtained by cutting pGEM-T-CMV-hGAD65-SV40pA with EagI and PvuI, to prepare pssAAV-GAD65.

In order to introduce the GAD65 expression cassette into pVAX1 (Invitrogen, USA), BamHI site was generated at the back of bGHpA by mutagenesis, which was then cut with MluI and NheI, to prepare DNA fragments. The LITR and CMV promoter regions were amplified by PCR using the pssAAV-GAD65 as a template, and cloned into pGEM-T easy (Promega, USA), which were then cut with AscI and NheI, and ligated to the pVAX1 vector prepared above, to prepare pVAX1-LITR-CMV. The primer sequences used for the amplification of LITR and CMV promoter regions are as follows.

```
F-ITR (SEQ ID NO: 22):
5'-ATGGCGCGCCCCTGGCCTTTTGCTGGCC-3'

R-JDK (SEQ ID NO: 17):
5'-GACGTCGACCTAGCTAGCGAATTCGGGGCCGCGGAG-3'
```

The pVAX1-LITR-CMV was prepared as a DNA fragment by cutting with NotI and NheI, and ligated to the DNA fragment prepared by cutting the pssAAV-GAD65 with EagI and NheI, to prepare pVAX1-LITR-CMV-hGAD65-SV40pA.

The pVAX1-LITR-CMV-hGAD65-SV40pA was cut with HpaI and BamHI, and then ligated to the DNA fragments obtained by treating the pGEM-T easy-SV40pA-RITR, which had been amplified by PCR using pssAAV-GAD65 as a template and cloned into pGEM-T easy, with HpaI and BamHI, to complete pVAX1-LITR-CMV-hGAD65-SV40pA-RITR (hereinafter, abbreviated as "pAAV-GAD65"). The primer sequences used for the amplification of SV40pA and RITR regions are as follows.

```
F-SV40pA (SEQ ID NO: 18):
5'-CCATCGATCAGACATGATAAGATACATTGATGAG-3'

R-ITR (SEQ ID NO: 23):
5'-ATGGATCCGCTAGTAAATACCGCATCAG-3'
```

The vector map of pAAV-hGAD65 is shown in FIG. 1.

B. Preparation of pAAV-rIL-10 pAAV-rIL-10 was prepared by a similar method to pAAV-hGAD65. Rat IL-10 gene was prepared by codon-optimization to fit for rats based on rat-derived base sequence (NCBI NM_012854) having the amino acid sequence of SEQ ID NO: 6 and synthesizing a gene having the base sequence of SEQ ID NO: 8 (Bioneer, Korea). The rIL-10 genes were amplified by PCR using the rat IL-10 genes introduced into pGEM-T easy as a template, and then treated with NheI and SalI to obtain a 0.5 Kb DNA fragment, which was then ligated to a 3.7 Kb DNA fragment obtained by cutting the pGEM-T-CMV with NheI and SalI, to prepare pGEM-T-CMV-rIL-10. The primer sequences used for the amplification of rIL10 is as follows.

```
F-rIL-10 (SEQ ID NO: 24):
5'-CCGCTAGCGCCACCATGCCT-3'

R-rIL-10 (SEQ ID NO: 25):
5'-GACGTCGACGCCATCGATGGCTTAATTAATCAATTCTTC-3'
```

SV40pA was amplified by performing PCR using pCI as a template, followed by treatment with NotI and SalI to obtain a 222 bp DNA fragment. The above fragment was ligated to a 4.2 Kb DNA fragment prepared by cutting pGEM-T-CMV-rIL-10 prepared above with ClaI and SalI, to prepare pGEM-T-CMV-rIL-10-SV40pA. The primer sequences used for the amplification of SV40pA are as follows.

```
F-SV40pA (SEQ ID NO: 18):
5'-CCATCGATCAGACATGATAAGATACATTGATGAG-3'

R-SV40pA (SEQ ID NO: 19):
5'-GACGTCGACGCGGCCGCTACCACATTTGTAGAGGTTTTACTTG-3'
```

A 1.6 Kb DNA fragment was obtained by treating pGEM-T-CMV-rIL-10-SV40pA with EagI, and then ligated to the DNA fragment prepared by treating pAAV-MCS-Kan$^r$ with NotI and BamHI, to prepare pssAAV-CMV-rIL-10-SV40pA (hereinafter, abbreviated as "pAAV-rIL-10"). The vector map of pAAV-rIL-10 is shown in FIG. 2.

C. Preparation of pAAV-rIL-4

The rat IL-4 gene was prepared by codon-optimization to fit for rats based on the rat-derived base sequence (NCBI NM_201270) having the amino acid sequence of SEQ ID NO: 11 and synthesizing a gene having the base sequence of SEQ ID NO: 13 (Bioneer, Korea). The rIL-4 genes introduced into pGEM-B1 (Bioneer, Korea) were treated with NheI and NotI to obtain a 0.5 Kb DNA fragment. The above fragment was ligated to a 3 Kb DNA fragment prepared by treating pAAV-hGAD65 with NheI and NotI, to prepare pssAAV-CMV-rIL-4-SV40pA (hereinafter, abbreviated as "pAAV-rIL-4"). The vector map of pAAV-rIL-4 is shown in FIG. 3.

D. Property Analysis of Recombinant Adeno-Associated Viruses

The three types of plasmids (pAAV-hGAD65, pAAV-rIL-10 and pAAV-rIL-4) prepared above were respectively transfected into 293T cells, a human embryonic kidney cell line, with pHelper and pRC using PEI (Polysciences, USA). Herein, pRC5 into which the capsid gene of AAV serotype 5 was introduced was used for hGAD65, while pRC1 into which the capsid gene of AAV serotype 1 was introduced was used for rIL-10 and rIL-4. The transfected cells were cultured in a 37° C. incubator, collected after 48 hours, and subjected to 3 cycles of freezing and thawing to obtain each crude virus.

In order to confirm the protein expression of the recombinant adeno-associated viruses delivered to the cells, 293T cells, a human embryonic kidney cell line, were respectively treated with crude viruses AAV5-hGAD65, AAV1-rIL-10 and AAV1-rIL-4, the protein expression was confirmed by Western blot. Specifically, $8 \times 10^5$ 293T cells were aliquoted into T25 flasks, and each flask was treated with 700 μL of crude viruses on the next day, followed by culturing in a 37° C. incubator. After 48 hours, the cells and the culture media were harvested separately, and the cells were dissolved with a solubilizing agent and the culture media were concentrated with amicon (Merck Millipore, Germany). The prepared samples were treated with the antibodies to GAD65 (Cell signaling, USA), IL-10 (Santa Cruz, USA) and IL-4 (Santa Cruz, USA), respectively, and subjected to Western blot. The results are shown in FIG. 4.

FIG. 4 is a diagram showing the expression of each protein by performing Western blot analysis of the cell lysates of 293T cell line, a human embryonic kidney cell line, treated with AAV5-hGAD65, AAV1-rIL-10 or AAV1-rIL-4. By confirming that a target protein was expressed in every case, it was confirmed that there was no problem in the structure and property of the recombinant adeno-associated viruses used in the experiment.

In order to confirm that GABA is produced by AAV5-hGAD65, the culture media of the cells treated with AAV5-GAD65 were collected under the same condition as that for sample preparation for Western blot, and subjected to GABA ELISA (LDN, Netherland) analysis. The results are shown in FIG. 5. Two identical samples were prepared separately for each experiment group, and the bar represents the value for each sample. As a result, it was confirmed that GABA was secreted into the culture medium by GAD65 introduced into the cells by AAV5-hGAD65 viruses.

E. Preparation of Recombinant Adeno-Associated Viruses

Recombinant adeno-associated viruses were prepared and purified by KRcrogen (Korea) for animal efficacy experiments, and the preparation method is as follows.

Three types of plasmids (pAAV-hGAD65, pAAV-rIL-10, and pAAV-rIL-4) prepared above were respectively transfected into 293T cells, a human embryonic kidney cell line, using calcium phosphate method with pHelper and pRC. Herein, pRC5 into which the capsid gene of AAV serotype 5 was introduced was used for hGAD65, while pRC1 into which the capsid gene of AAV serotype 1 was introduced was used for rIL-10 and rIL-4. The transfected cells were cultured in a 37° C. incubator, and collected after 48 hours.

Then, only the bands containing viruses were isolated and purified through high-speed centrifugation depending on cesium concentration gradient, to obtain AAV5-hGAD65, AAV1-rIL-10 and AAV1-rIL-4. The titers of the produced viruses were measured using qPCR method established by the manufacturer.

Example 2

Analgesic Efficacy Test of AAV-IL-10 and AAV-GAD65

A. Preparation of Administration Samples 30 minutes before the animal administration, the recombinant adeno-associated virus stored at −80° C. were thawed at room temperature within 1 minute and mixed well by vortex. And Coomassie blue dye solution was prepared by mixing 10 mg of Coomassie blue in 1 mL of PBS well, and then filtering by syringe filters. 1 µL of AAV-GAD65 of $5.4 \times 10^5$ VG/µL, 1 µL of AAV-IL-10 of $1.8 \times 10^7$ VG/µL and 1 µL of 0.1% Coomassie blue dye were mixed under the calculation that each animal gets 3 µL in total. The samples were prepared twice as much as the amount required, and 3 µL of the sample was administered to each animal.

As a control group, Gabapentin was mixed in animals' drinking water 1 hour prior to administration, which was prepared in a concentration of 10 mg/mL.

B. Preparation of Neuropathic Pain Animal Model and Sample Administration

Male SD-rats of 180 to 200 g were anesthetized with inhalation anesthesia, and then upper parts of the calves were incised, and both ends of the common peroneal nerve and tibial nerve were tied and knots were made by 7-0 suture at 0.5-1 cm intervals. The regions of the two nerve bundles between the knots were cut by scissors and the incision site was sutured. Two weeks later, von Frey filament test was performed to confirm pain induction, and then the test substance was administered (C. J. Woolf, *Pain* 87, 2000).

The test substance was administered to dorsal root ganglion (DRG). After inhalation anesthesia of the pain animal model, rat's back at the lumbar spine from L3 to L5 was linearly incised to expose vertebral bones, and then a transverse process, one of the spinal projections, was exposed at the side of the exposure, and the L4 process covering the DRG in the fixed state was carefully separated under the Stereo zoom microscopic view by a rongeur such that the DRG is not damaged. The area around the DRG was manipulated so that the DRG which extends in an oblique line was exposed like grains of rice.

A hamilton syringe was connected to a polyethylene catheter, and 3 µL of the test substance was accurately collected. Then, the syringe was replaced with a 1 mL syringe for the administration. The rats were placed on a small animal stereotaxic instrument, and the sample was injected while confirming that the micro-needle was pricking the L4 DRG accurately under a surgioscope. Herein, it was confirmed that the sample containing dye did not leak out of the DRG and was well delivered to the inside of the DRG. After confirming that entire sample was delivered to the DRG, the syringe was separated from the DRG, and suturing was done, and the animals were recovered.

Gabapentin was orally administered with 3 mg/kg.

C. Observation of Analgesic Efficacy Using von Frey Filament Test

The 50% up & down threshold method established by Dixon in 1992 was employed since it is a commonly known method. The method calculates threshold values depending on a predetermined patterns of pain responses with a total of 8 filaments whose N values were 0.4, 0.6, 1, 2, 4, 6, 8 and 15 g, respectively. Pain occurrence regions were searched through changing positions from the region of most lateral toe to the heel of the sole where pain has occurred.

Rats abruptly lift the soles and shrink or lick the soles when pain occurs. Accordingly, when pain occurring region was found, the surrounding area was pricked 5 times with the filament of the next step and if there were responses for 3 times or more, it was regarded as a pain response, and the rats were observed with the filament of the next step. Patterns were recorded at every step. The pain patterns were recorded based on the pattern table established by S. R. Chaplan (Quantitative assessment of tactile allodynia in the rat paw. *Journal of Neuroscience Methods,* 1994) and the threshold values were calculated using it. The behavior analysis of the animal groups is performed by a blind method for 4 to 6 weeks, observed by at least 3 people, and the results of the recorded patterns are statistically processed to analyze the tendency of pain.

The results of pain-observation employing von Frey filament test where the pain animal model was administered with samples are shown in FIG. 6. FIG. 6 shows the results of comparing the efficacies between co-administration of AAV-GAD65 and AAV-IL-10 and gabapentin administration. When GAD65 and IL-10 were co-administered, statistically significant pain-relieving effect was observed as compared to the untreated control group (negative control), and the effect was found to be higher than that of Gabapentin.

Example 3

Analgesic Efficacy Tests of AAV-IL-10 and AAV-GAD65

A. Preparation of Administration Samples

For the preparation of administration samples, rAAV5-GAD65 and rAAV1-rIL-10 which were prepared in Example 1 and stored in a frozen state were thawed, and samples were prepared in accordance with substantially the same method as the preparation method of administration samples in Example 2. Specifically, the single administration substance AAV-GAD65 or AAV-rIL-10 and the co-administration substances AAV-GAD65 and AAV-rIL-10 were diluted in PBS in a virus titer-based mixing ratio of 1:1, 1:5, or 1:30 as shown in Table 1, and 1 µL of 0.1% Coomassie blue dye was added to each sample under the calculation that each animal gets 3 µL. The samples were prepared twice as much as the amount required for the total population, and 3 µL of the sample was administered to each animal.

TABLE 1

| Samples | Virus types and contents | |
|---|---|---|
| | AAV-GAD65 | AAV-IL-10 |
| Comparative Example 1 (GAD alone) | $5.4 \times 10^5$ VG/2 µL | 0 |
| Comparative Example 2 (IL-10 alone) | 0 | $1.8 \times 10^7$ VG/2 µL |
| Experimental Example 1 (1:1) | $5.4 \times 10^5$ VG/1 µL | $5.4 \times 10^5$ VG/1 µL |
| Experimental Example 2 (1:5) | $5.4 \times 10^5$ VG/1 µL | $2.7 \times 10^6$ VG/1 µL |
| Experimental Example 3 (1:30) | $5.4 \times 10^5$ VG/1 µL | $1.8 \times 10^7$ VG/1 µL |

B. Observation of Analgesic Efficacy Using von Frey Filament Test

Samples were administered to the pain animal models prepared by the same method as in Example 2, and pain was observed using a von Frey filament test, and the results are shown in FIG. 7.

FIG. 7 illustrates efficacies of AAV-GAD65 and AAV-IL-10 depending on composition ratios thereof. Particularly, compared to trace amounts of AAV-GAD65 and AAV-rIL-10 which showed no analgesic efficacy experiments with the mixing composition ratios of AAV-rIL-10 to AAV-GAD of 1:1 (Experimental Example 1), 1:5 (Experimental Example 2) and 1:30 (Experimental Example 3) exhibited synergistic efficacies in animal behavior analysis. As a result, the co-administration composition of AAV-GAD65 and AAV-rIL-10 according to the present invention showed an increasing pattern of the pain treatment efficacy as the mixing composition ratio of AAV-rIL-10 to AAV-GAD increased.

Example 4

Analgesic Efficacy Tests of AAV-IL-10 and AAV-GAD65 Using Transforaminal Epidural Injection A. Preparation of Administration Samples 30 minutes before the animal administration experiment, the reagents kept at −80° C. were thawed at room temperature within 1 minute and mixed well by vortex. AAV-GAD65 and AAV-IL-10 were diluted in PBS to obtain the viral titers shown in Table 2. In order to administer 5 µL of the sample to each animal, the two virus diluted solutions were mixed half and half to obtain 1.5 times the volume required. Then, 5 µL of the sample was administered to each animal.

TABLE 2

| Samples | Virus types and contents | |
|---|---|---|
| | AAV-GAD65 | AAV-IL-10 |
| Experimental Example1 (1:10) | $5.0 \times 10^6$ VG/2.5 µL | $5.0 \times 10^7$ VG/2.5 µL |
| Experimental Example2 (1:30) | $5.0 \times 10^6$ VG/2.5 µL | $1.5 \times 10^8$ VG/2.5 µL |

B. Preparation of Neuropathic Pain Model and Sample Administration

The neuropathic pain animal model was prepared by the same method as described in Example 2, and then the test substance was administered.

The test substance was administered by transforaminal epidural injection method at a position adjacent to the dorsal root ganglion (DRG). After inhalation anesthesia of the neuropathic pain animal model, rat's back at the lumbar spine from L3 to L5 was linearly incised to expose vertebral bones, and then, L4 transverse process, one of the spinal projections, was exposed at the side of the exposure. The rat was laid down sideways such that its side aspect could be seen from above, so that the L4 intervertebral foramen is visible.

A micro needle attached to the catheter was put into the prepared sample. A Hamilton syringe was connected to the opposite end of the catheter and pulled until reaching the marking of 5 µL to inject the sample into the catheter. After removing the Hamilton syringe from the catheter, the region at 1 cm from the tip of the needle was gripped by Halsted-Mosquito. As L4 spine was gripped by forceps and pulled upward, the tip area of the needle fixed by Halsted-Mosquito Straight was placed around the L4 intervertebral foramen. The tip of the needle was inserted into the intervertebral foramen whose space was secured, and advanced until the needle reached a bent portion inside the intervertebral foramen, and the needle which had been gripped was released. After confirming that the needle is fixed, a 1 mL syringe was connected to the polyethylene catheter connected to the opposite side of the needle. The piston was gently pressed to slowly administer the diluted administration substance to the rat DRG surrounding area, followed by suturing, to complete the administration procedure. By the same method as described in Example 2, pain results employing the von Frey filament test were observed at 4 weeks after administration of the substance. The results are shown in FIG. 8.

FIG. 8 shows that a mixture of AAV-GAD65 and AAV-IL-10 exhibits efficacy even when administered by the transforaminal epidural injection method. In addition, synergistic efficacy in animal behavior analysis was confirmed at the mixed composition ratio of AAV-GAD65 to AAV-IL-10 of 1:10 (Experimental Example 1) and 1:30 (Experimental Example 2).

Example 5

Comparison of Efficacies of AAV-GAD65 and AAV-IL-10 with AAV-GAD65 and AAV-IL-4

A pain animal model was prepared by substantially the same method as in Example 2, and the preparation procedure of the administration sample was the same as well. AAV1-rIL-4 described in Example 1 was thawed and prepared for use in animal experiments as follows.

30 minutes before animal DRG administration experiment, the reagents stored at −80° C. were thawed at room temperature within 1 minute and mixed well by vortex. 10 mg of Coomassie blue was mixed well in 1 mL of PBS, and then, dyes filtered by syringe filters were prepared. AAV-GAD65 and AAV-rIL-4 were diluted in PBS to obtain the virus titer-based mixing ratios shown in Table 3, and 1 μL of 0.1% Coomassie blue dye was added to each sample under the calculation that each animal gets 3 μL. The samples were prepared twice as much as the amount required for the total population, and 3 μL of the sample was administered to each animal.

TABLE 3

| | Virus types and contents | | |
|---|---|---|---|
| Samples | AAV-GAD65 | AAV-IL-10 | AAV-IL-4 |
| Comparative Example 1 | $5.4 \times 10^5$ VG/2 μL | — | — |
| Comparative Example 2 | — | $1.8 \times 10^7$ VG/2 μL | — |
| Comparative Example 3 | — | — | $1.8 \times 10^7$ VG/2 μL |
| Comparative Example 4 | $5.4 \times 10^5$ VG/1 μL | — | $1.8 \times 10^7$ VG/1 μL |
| Experimental Example 1 | $5.4 \times 10^5$ VG/1 μL | $1.8 \times 10^7$ VG/1 μL | — |

The pain results employing the von Frey filament test were observed, and the results are shown in FIG. 9. The FIG. 9 shows the results of comparing the efficacies of AAV-GAD65 and AAV-rIL-10 with AAV-GAD65 and AAV-rIL-4, which illustrates the synergistic efficacies comparatively appearing in animal behavior analysis when IL-10 and IL-4, cytokines having anti-inflammatory effects, were used in combination with GAD65, respectively. As shown in FIG. 9, the pain treatment efficacy was insignificant or not observed when GAD65, IL-10 or IL-4 was administered alone, and no significant analgesic efficacy was observed when GAD65 and IL-4 were co-administered as compared to the cases where GAD65 or IL-4 was administered alone. On the other hand, when GAD65 and IL-10 were co-administered, it was confirmed that there was higher analgesic efficacy which was statistically significant than the other comparative examples. In particular, synergistic pain-relieving effect was observed, which was not shown when GAD65 and IL-4 were co-administered.

The invention claimed is:

1. A method for relieving or treating pain in a subject with pain comprising administering a composition to the subject, wherein the composition comprises (a) a first vector comprising a gene encoding glutamate decarboxylase (GAD); and (b) a second vector comprising a gene encoding interleukin-10 (IL-10), wherein the gene encoding GAD and the gene encoding IL-10 are operably linked to expression control sequences;

wherein the administering the composition relieves the pain, wherein the pain is nociceptive pain, inflammatory pain, or pathological pain; and wherein the composition is directly administered to a central nervous system of the subject.

2. The method of claim 1, wherein the pain is neuropathic pain, cancer pain, postoperative pain, trigeminal neuralgia, idiopathic pain, diabetic neuropathic pain, or migraine.

3. The method of claim 1, wherein the first vector and the second vector are each a viral vector selected from the group consisting of adenovirus, adeno-associated virus (AAV), herpes simplex virus, lentivirus, retrovirus, and poxvirus; and wherein a ratio of vector genomes (VG) of the first vector per µl of the composition and vector genomes (VG) of the second vector per µl of the composition is 1:1 to 1:50.

4. The method of claim 1, wherein the GAD is one or more selected from the group consisting of GAD65 and GAD67.

5. The method of claim 1, wherein the GAD consists of the amino acid sequence of SEQ ID NO: 1 or SEQ ID NO: 4.

6. The method of claim 1, wherein the gene encoding GAD consists of the nucleotide sequence of SEQ ID NO: 2, SEQ ID NO: 3, or SEQ ID NO: 5.

7. The method of claim 1, wherein the IL-10 consists of the amino acid sequence of SEQ ID NO: 6 or SEQ ID NO: 9.

8. The method of claim 1, wherein the gene encoding IL-10 consists of the nucleotide sequence of SEQ ID NO: 7, SEQ ID NO: 8 or SEQ ID NO: 10.

9. The method of claim 1, wherein the composition further comprises a physiologically acceptable carrier.

10. The method of claim 1, wherein the composition is suitable for an injection.

\* \* \* \* \*

```
SEQUENCE LISTING

<160> NUMBER OF SEQ ID NOS: 25

<210> SEQ ID NO 1
<211> LENGTH: 585
<212> TYPE: PRT
<213> ORGANISM: Homo sapiens

<400> SEQUENCE: 1

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
```

```
                115                 120                 125
Ser Thr Lys Val Ile Asp Phe His Tyr Pro Asn Glu Leu Leu Gln Glu
            130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
    355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540
```

```
Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 2
<211> LENGTH: 2824
<212> TYPE: DNA
<213> ORGANISM: Homo sapiens

<400> SEQUENCE: 2
gcggccgccc gcacttcccg cctctggctc gcccgaggac gcgctggcac gcctcccacc      60
ccctcactct gactccagct ggcgtgcatg gtctgcctcg catcctcacg actcagctcc     120
ctccctctct cgtgtttttt tcctccgccg cccctcatt catccccact gggctccctt      180
tccctcaaat gctctggggc tctccgcgct ttcctgagtc cgggctccga ggacccttag     240
gtagtcccgg tctctttta agctccccgg cttccaaagg gttgccacgt ccctaaaccc     300
tgtctccagc tcgcatacac acacgcacag acacgcacgt tttctgttcc tgcgtgacac     360
ccgccctcgc cgctcggccc cgccggtccc cgcgcggtgc cctcctcccg ccacacgggc     420
acgcacgcgc gcgcagggcc aagcccgagg cagctcgccc gcagctcgca ctcgcaggcg     480
acctgctcca gtctccaaag ccgatggcat ctccgggctc tggcttttgg tctttcgggt     540
cggaagatgg ctctggggat tccgagaatc ccggcacagc gcgagcctgg tgccaagtgg     600
ctcagaagtt cacgggcggc atcggaaaca aactgtgcgc cctgctctac ggagacgccg     660
agaagccggc ggagagcggc gggagccaac ccccgcgggc cgccgcccgg aaggccgcct     720
gcgcctgcga ccagaagccc tgcagctgct ccaaagtgga tgtcaactac gcgtttctcc     780
atgcaacaga cctgctgccg gcgtgtgatg agaaaggcc cactttggcg tttctgcaag     840
atgttatgaa cattttactt cagtatgtgg tgaaaagttt cgatagatca accaaagtga     900
ttgatttcca ttatcctaat gagcttctcc aagaatataa ttgggaattg gcagaccaac     960
cacaaaattt ggaggaaatt ttgatgcatt gccaaacaac tctaaaatat gcaattaaaa    1020
cagggcatcc tagatacttc aatcaacttt ctactggttt ggatatggtt ggattagcag    1080
cagactggct gacatcaaca gcaaatacta acatgttcac ctatgaaatt gctccagtat    1140
ttgtgctttt ggaatatgtc acactaaaga aaatgagaga atcattggc tggccagggg    1200 gctctggcga tgggatattt ctcccggtg gcgccatatc taacatgtat gccatgatga    1260
tcgcacgctt taagatgttc ccagaagtca aggagaaagg aatggctgct cttcccaggc    1320
tcattgcctt cacgtctgaa catagtcatt tttctctcaa gaagggagct gcagccttag    1380
ggattggaac agacacgcgtg attctgatta aatgtgatga gagagggaaa atgattccat    1440
ctgatcttga aagaaggatt cttgaagcca aacagaaagg gtttgttcct ttcctcgtga    1500
gtgccacagc tggaaccacc gtgtacggag catttgaccc cctcttagct gtcgctgaca    1560
tttgcaaaaa gtataagatc tggatgcatg tggatgcagc ttgggtggg ggattactga    1620 tgtcccgaaa acacaagtgg aaactgagtg gcgtggagag ggccaactct gtgacgtgga    1680
atccacacaa gatgatggga gtccctttgc agtgctctgc tctcctggtt agagaagagg    1740
gattgatgca gaattgcaac caaatgcatg cctcctacct ctttcagcaa gataacatt     1800 atgacctgtc ctatgacact ggagacaagg ccttacagtg cggacgccac gttgatgttt    1860
```

```
ttaaactatg gctgatgtgg agggcaaagg ggactaccgg gtttgaagcg catgttgata    1920
aatgtttgga gttggcagag tatttataca acatcataaa aaaccgagaa ggatatgaga    1980
tggtgtttga tgggaagcct cagcacacaa atgtctgctt ctggtacatt cctccaagct    2040
tgcgtactct ggaagacaat gaagagagaa tgagtcgcct ctcgaaggtg gctccagtga    2100
ttaaagccag aatgatggag tatggaacca caatggtcag ctaccaaccc ttgggagaca    2160
aggtcaattt cttccgcatg gtcatctcaa acccagcggc aactcaccaa gacattgact    2220
tcctgattga agaaatagaa cgccttggac aagatttata ataaccttgc tcaccaagct    2280
gttccacttc tctagagaac atgccctcag ctaagccccc tactgagaaa cttcctttga    2340
gaattgtgcg acttcacaaa atgcaaggtg aacaccactt tgtctctgag aacagacgtt    2400
accaattatg gagtgtcacc agctgccaaa atcgtaggtg ttggctctgc tggtcactgg    2460
agtagttgct actcttcaga atatggacaa agaaggcaca ggtgtaaata tagtagcagg    2520
atgaggaacc tcaaactggg tatcattttg cacgtgctct tctgttctca aatgctaaat    2580
gcaaacactg tgtatttatt agttaggtgt gccaaactac cgttcccaaa ttggtgtttc    2640
tgaatgacat caacattccc ccaacattac tccattacta aagacagaaa aaaataaaaa    2700
cataaaatat acaaacatgt ggcaacctgt tcttcctacc aaatataaac ttgtgtatga    2760
tccaagtatt ttatctgtgt tgtctctcta aacccaaata aatgtgtaaa tgtggacaca    2820
tctc                                                                2824

<210> SEQ ID NO 3
<211> LENGTH: 1758
<212> TYPE: DNA
<213> ORGANISM: Artificial Sequence
<220> FEATURE:
<223> OTHER INFORMATION: Optimized human GAD65

<400> SEQUENCE: 3
atggcatctc cgggctccgg cttttggtcc ttcgggtcgg aagatggctc aggggattcc      60
gagaatcccg gcacagcgcg gcctggtgt caagtggctc agaagttcac gggcggcatc     120
ggaaacaaac tgtgtgccct gctctacggc gacgccgaga gcccgcagag agcggcggg     180 agccaacccc gcgggccgc cgcccggaag gccgcctgcg cctgtgacca gaagccctgc     240
tcatgcagca aggtagatgt caactacgcg tttctccatg ccacagatct gctgccggct     300
tgcgacggtg aaaggcccac tttggccttt ctgcaggatg ttatgaacat tctgctgcag     360
tacgtggtga aaagtttcga ccggtcaacc aaagtgatcg actttcacta tcctaatgaa     420
cttctccagg agtacaattg ggagctggct gaccagccac agaacctgga ggaaatcttg     480
atgcattgcc aaactactct aaaatatgca attaaaacag gccatcctag atacttcaac     540 cagcttttcta ccggtttgga tatggtgggg ctggcagccg actggctgac atccaccgca     600
aataccaaca tgttcaccta tgagatcgct cctgtcttcg tgcttttgga atacgtcacc     660
ctaaagaaga tgcgtgaaat cattggctgg ccaggaggct ctggtgatgg tatatttttct     720 cccggcggcg cgatctctaa catgtatgcc atgatgatcg cacgctttaa gatgttccca     780
gaagtcaagg agaaaggaat ggctgctctt cccaggctca ttgccttcac gagtgaacac     840
agtcactttt ccctcaagaa gggggctgcc gccttaggga tcggaacaga cagcgtgatt     900
ctgataaagt gcgacgagag agggaaaatg attccatctg atcttgagag aaggattctt     960
gaagccaaac agaaagggtt tgtccctttc ctcgtgagtg ccacagctgg aaccaccgtg    1020
```

```
tacggcgcat ttgacccct cttagctgtc gcggatatat gtaagaagta taagatctgg      1080
atgcacgtgg atgctgcttg ggtgggggga ttactgatgt ccaggaaaca caagtggaaa      1140
ctgtctggcg tggagcgcgc aacagcgtg acgtggaatc cacacaaaat gatgggagtc      1200
cctttgcagt gctctgctct cctggttcga agagggac tgatgcagaa ttgcaaccaa      1260
atgcatgcct cctacctctt tcagcaggat aaacattatg acctgtctta cgacactggt      1320
gacaaggccc tgcagtgtgg cgccacgtt gatgtattca agctatggct gatgtggagg      1380
gcaaagggga ctaccggttt tgaagcccat gttgacaaat gtctggagtt ggcagagtat      1440
ttatacaata tcataaaaaa ccgagaagga tatgagatgg tgtttgatgg caagcctcag      1500
cacacaaatg tctgcttctg gtacatccct cccagcctac gtactctgga ggacaacgaa      1560
gagagaatga gtcgcctctc gaaggtggct ccagtgatta aagccagaat gatggagtat      1620
ggaaccacaa tggtcagcta ccaaccttg ggggacaagg taaatttctt ccgcatggtc      1680
atctcaaacc cagcggcaac tcaccaagac attgatttcc tgattgaaga gatcgagcgg      1740
ctcggccagg atctgtga                                                   1758
```

<210> SEQ ID NO 4
<211> LENGTH: 594
<212> TYPE: PRT
<213> ORGANISM: Homo sapiens

<400> SEQUENCE: 4

```
Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
    50                  55                  60

Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240
```

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
        275                 280                 285

Gln Ser His Tyr Ser Ile Lys Lys Ala Gly Ala Ala Leu Gly Phe Gly
    290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
        355                 360                 365

Trp Leu His Val Asp Ala Ala Trp Gly Gly Gly Leu Leu Met Ser Arg
    370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Phe Gln Pro Asp Lys Gln Tyr Asp Val Ser Tyr Asp Thr
        435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu

<210> SEQ ID NO 5
<211> LENGTH: 1784
<212> TYPE: DNA
<213> ORGANISM: Homo sapiens

<400> SEQUENCE: 5
atggcgtctc gacccatct tcgtccgcaa cctcctcgaa cgcgggagcg gaccccaata        60 ccactaaccct gcgccccaca acgtacgata cctggtgcgg cgtggcccat ggatgcacca       120

```
gaaaactggg gctcaagatc tgcggcttct tgcaaaggac caacagcctg gaagagaaga      180
gtcgccttgt gagtgccttc aaggagaggc aatcctccaa gaacctgctt tcctgtgaaa      240
acagcgaccg ggatgcccgc ttccggcgca cagagactga cttctctaat ctgtttgcta      300
gagatctgct tccggctaag aacggtgagg agcaaaccgt gcaattcctc ctggaagtgg      360
tggacatact cctcaactat gtccgcaaga catttgatcg ctccaccaag gtgctggact      420
ttcatcaccc acaccagttg ctggaaggca tggagggctt caacttggag ctctctgacc      480
accccgagtc cctggagcag atcctggttg actgcagaga caccttgaag tatggggttc      540
gcacaggtca tcctcgattt ttcaaccagc tctccactgg attggatatt attggcctag      600
ctggagaatg gctgacatca acggccaata ccaacatgtt tacatatgaa attgcaccag      660
tgtttgtcct catggaacaa ataacactta agaagatgag agagatagtt ggatggtcaa      720
gtaaagatgg tgatgggata ttttctcctg ggggcgccat atccaacatg tacagcatca      780
tggctgctcg ctacaagtac ttcccggaag ttaagacaaa gggcatggcg gctgtgccta      840
aactggtcct cttcacctca gaacagagtc actattccat aaagaaagct ggggctgcac      900 ttggcttttgg aactgacaat gtgattttga taaagtgcaa tgaaaggggg aaaataattc      960
cagctgattt tgaggcaaaa attcttgaag ccaaacagaa gggatatgtt ccctttttatg     1020 tcaatgcaac tgctggcacg actgtttatg gagcttttga tccgatacaa gagattgcag     1080
atatatgtga gaaatataac ctttggttgc atgtcgatgc tgcctgggga ggtgggctgc     1140
tcatgtccag gaagcaccgc cataaactca acggcataga aagggccaac tcagtcacct     1200
ggaaccctca caagatgatg ggcgtgctgt tgcagtgctc tgccattctc gtcaaggaaa     1260
agggtatact ccaaggatgc aaccagatgt gtgcaggata cctcttccag ccagacaagc     1320
agtatgatgt ctcctacgac accggggaca aggcaattca gtgtggccgc cacgtggata     1380
tcttcaagtt ctggctgatg tggaaagcaa agggcacagt gggatttgaa accagatca      1440 acaaatgcct ggaactggct gaataccTct atgccaagat taaaaacaga gaagaatttg     1500
agatggtttt caatggcgag cctgagcaca caaacgtctg tttttggtat attccacaaa     1560
gcctcagggg tgtgccagac agccctcaac gacgggaaaa gctacacaag gtggctccaa     1620
aaatcaaagc cctgatgatg gagtcaggta cgaccatggt tggctaccag ccccaagggg     1680
acaaggccaa cttcttccgg atggtcatct ccaacccagc cgctacccag tctgacattg     1740
acttcctcat tgaggagata gaaagactgg gccaggatct gtaa                      1784
```

<210> SEQ ID NO 6
<211> LENGTH: 178
<212> TYPE: PRT
<213> ORGANISM: Rattus norvegicus

<400> SEQUENCE: 6

Met Pro Gly Ser Ala Leu Leu Cys Cys Leu Leu Leu Leu Ala Gly Val
1               5                   10                  15

Lys Thr Ser Lys Gly His Ser Ile Arg Gly Asp Asn Asn Cys Thr His
                20                  25                  30

Phe Pro Val Ser Gln Thr His Met Leu Arg Glu Leu Arg Ala Ala Phe
            35                  40                  45

Ser Gln Val Lys Thr Phe Phe Gln Lys Lys Asp Gln Leu Asp Asn Ile
        50                  55                  60

Leu Leu Thr Asp Ser Leu Leu Gln Asp Phe Lys Gly Tyr Leu Gly Cys
65                  70                  75                  80

Gln Ala Leu Ser Glu Met Ile Lys Phe Tyr Leu Val Glu Val Met Pro
                85                  90                  95

Gln Ala Glu Asn His Gly Pro Glu Ile Lys Glu His Leu Asn Ser Leu
            100                 105                 110

Gly Glu Lys Leu Lys Thr Leu Trp Ile Gln Leu Arg Arg Cys His Arg
        115                 120                 125

Phe Leu Pro Cys Glu Asn Lys Ser Lys Ala Val Glu Gln Val Lys Asn
    130                 135                 140

Asp Phe Asn Lys Leu Gln Asp Lys Gly Val Tyr Lys Ala Met Asn Glu
145                 150                 155                 160

Phe Asp Ile Phe Ile Asn Cys Ile Glu Ala Tyr Val Thr Leu Lys Met
                165                 170                 175

Lys Asn

<210> SEQ ID NO 7
<211> LENGTH: 682
<212> TYPE: DNA
<213> ORGANISM: Rattus norvegicus

<400> SEQUENCE: 7
catgcctggc tcagcactgc tatgttgcct gctcttactg gctggagtga agaccagcaa      60
aggccattcc atccggggtg acaataactg cacccacttc ccagtcagcc agacccacat     120
gctccgagag ctgagggctg ccttcagtca agtgaagact ttcttcaaa agaaggacca     180 gctggacaac atactgctga cagattcctt actgcaggac tttaagggtt acttgggttg     240
ccaagccttg tcagaaatga tcaagtttta cctggtagaa gtgatgcccc aggcagagaa     300
ccatggccca gaaatcaagg agcatttgaa ttccctggga gagaagctga gaccctctg     360 gatacagctg cgacgctgtc atcgatttct ccctgtgag aataaaagca aggcagtgga     420
gcaggtgaag aatgatttta ataagctcca agacaaaggt gtctacaagg ccatgaatga     480
gtttgacatc ttcatcaact gcatagaagc ctacgtgaca ctcaaaatga aaaattgaac     540
cacccggcat ctactggact gcaggacata aatagagctt ctaaatctga tccagagatc     600
ttagctaacg ggagcaactc cttggaaaac ctcgtttgta cctctctcca aaatatttat     660
tacctctgat acctcagttc cc                                             682

<210> SEQ ID NO 8
<211> LENGTH: 537
<212> TYPE: DNA
<213> ORGANISM: Artificial Sequence
<220> FEATURE:
<223> OTHER INFORMATION: Optimized rat IL-10

<400> SEQUENCE: 8
atgcctggct cagccctgct atgttgcctt ctcctgctgg cgggagtcaa gacaagcaag      60
ggccattcca tccggggaga taataactgc acccacttcc cagtctctca aacccacatg     120
ttgcgagagc tgagggctgc cttcagtcag gtgaagacgt tcttccagaa gaaggaccag     180
ctggacaaca ttctgctgac tgacagcctg ctgcaggatt caagggtta tttggggtgt     240 caagccctgt ctgaaatgat caagttttac ctggtagaag tgatgcccca ggcagagaat     300
catggccccg agatcaagga gcacctcaac tccctggggg agaagctgaa gaccctgtgg     360
attcagctga gcgctgcca gatttctc ccctgtgaaa acaagagcaa ggcagtggag     420
caggtgaaga cgattttaa taagctccag gacaagggcg tctacaaggc catgaacgag     480
ttcgacatct ttatcaactg catagaagct tacgttacac tcaagatgaa gaattga    537

<210> SEQ ID NO 9
<211> LENGTH: 178
<212> TYPE: PRT
<213> ORGANISM: Homo sapiens

<400> SEQUENCE: 9

```
Met His Ser Ser Ala Leu Leu Cys Cys Leu Val Leu Leu Thr Gly Val
1               5                  10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 10
<211> LENGTH: 1600
<212> TYPE: DNA
<213> ORGANISM: Homo sapiens

<400> SEQUENCE: 10
aaaccacaag acagacttgc aaaagaaggc atgcacagct cagcactgct ctgttgcctg     60
gtcctcctga ctggggtgag ggccagccca ggccagggca cccagtctga aacagctgc    120
acccacttcc caggcaacct gcctaacatg cttcgagatc tccgagatgc cttcagcaga    180
gtgaagactt tctttcaaat gaaggatcag ctggacaact tgttgttaaa ggagtccttg    240
ctggaggact taagggtta cctgggttgc caagccttgt ctgagatgat ccagttttac    300
ctggaggagg tgatgcccca agctgagaac aagacccag acatcaaggc gcatgtgaac    360
tccctggggg agaacctgaa gaccctcagg ctgaggctac ggcgctgtca tcgatttctt    420
ccctgtgaaa acaagagcaa ggccgtggag caggtgaaga atgcctttaa taagctccaa    480
gagaaaggca tctacaaagc catgagtgag tttgacatct tcatcaacta catagaagcc    540
tacatgacaa tgaagatacg aaactgagac atcagggtgg cgactctata gactctagga    600
cataaattag aggtctccaa aatcggatct ggggctctgg gatagctgac ccagccccctt   660
gagaaaccct attgtacctc tcttatagaa tatttattac ctctgatacc tcaaccccca    720
tttctatttta tttactgagc ttctctgtga acgatttaga aagaagccca atattataat    780

| | |
|---|---|
| tttttttcaat atttattatt ttcacctgtt tttaagctgt ttccataggg tgacacacta | 840 |
| tggtatttga gtgttttaag ataaattata agttacataa gggaggaaaa aaaatgttct | 900 |
| ttggggagcc aacagaagct tccattccaa gcctgaccac gctttctagc tgttgagctg | 960 |
| ttttccctga cctccctcta atttatcttg tctctgggct tggggcttcc taactgctac | 1020 |
| aaatactctt aggaagagaa accagggagc ccctttgatg attaattcac cttccagtgt | 1080 |
| ctcggaggga ttcccctaac ctcattcccc aaccacttca ttcttgaaag ctgtggccag | 1140 |
| cttgttattt ataacaacct aaatttggtt ctaggccggg cgcggtggct cacgcctgta | 1200 |
| atcccagcac tttgggaggc tgaggcgggt ggatcacttg aggtcaggag ttcctaacca | 1260 |
| gcctggtcaa catggtgaaa ccccgtctct actaaaaata caaaaattag ccgggcatgg | 1320 |
| tggcgcgcac ctgtaatccc agctacttgg gaggctgagg caagagaatt gcttgaaccc | 1380 |
| aggagatgga agttgcagtg agctgatatc atgcccctgt actccagcct gggtgacaga | 1440 |
| gcaagactct gtctcaaaaa ataaaaataa aaataaattt ggttctaata gaactcagtt | 1500 |
| ttaactagaa tttattcaat tcctctggga atgttacatt gtttgtctgt cttcatagca | 1560 |
| gattttaatt ttgaataaat aaatgtatct tattcacatc | 1600 |

<210> SEQ ID NO 11
<211> LENGTH: 147
<212> TYPE: PRT
<213> ORGANISM: Rattus norvegicus

<400> SEQUENCE: 11

Met Gly Leu Ser Pro His Leu Ala Val Thr Leu Phe Cys Phe Leu Ile
1               5                   10                  15

Cys Thr Gly Asn Gly Ile His Gly Cys Asn Asp Ser Pro Leu Arg Glu
            20                  25                  30

Ile Ile Asn Thr Leu Asn Gln Val Thr Glu Lys Gly Thr Pro Cys Thr
        35                  40                  45

Glu Met Phe Val Pro Asp Val Leu Thr Ala Thr Arg Asn Thr Thr Glu
    50                  55                  60

Asn Glu Leu Ile Cys Arg Ala Ser Arg Val Leu Arg Lys Phe Tyr Phe
65                  70                  75                  80

Pro Arg Asp Val Pro Pro Cys Leu Lys Asn Lys Ser Gly Val Leu Gly
                85                  90                  95

Glu Leu Arg Lys Leu Cys Arg Gly Val Ser Gly Leu Asn Ser Leu Arg
            100                 105                 110

Ser Cys Thr Val Asn Glu Ser Thr Leu Thr Leu Lys Asp Phe Leu
        115                 120                 125

Glu Ser Leu Lys Ser Ile Leu Arg Gly Lys Tyr Leu Gln Ser Cys Thr
    130                 135                 140

Ser Met Ser
145

<210> SEQ ID NO 12
<211> LENGTH: 475
<212> TYPE: DNA
<213> ORGANISM: Rattus norvegicus

<400> SEQUENCE: 12

| | |
|---|---|
| tctcacgtca ctgactgtag agagctattg atgggtctca gcccccacct tgctgtcacc | 60 |
| ctgttctgct ttctcatatg taccgggaac ggtatccacg gatgtaacga cagccctctg | 120 |
| agagagatca tcaacacttt gaaccaggtc acagaaaaag ggactccatg caccgagatg | 180 |

```
tttgtaccag acgtccttac ggcaacaagg aacaccacgg agaacgagct catctgcagg    240
gcttccaggg tgcttcgcaa attttacttc ccacgtgatg tacctccgtg cttgaagaac    300
aagtctgggg ttctcggtga actgaggaaa ctctgtagag gtgtcagcgg tctgaactca    360
ctgagaagct gcaccgtgaa tgagtccacg ctcacaacac tgaaagactt cctggaaagc    420
ctaaaaagca tcctacgagg gaaatacttg cagtcctgca cttccatgtc ctaac         475
```

<210> SEQ ID NO 13
<211> LENGTH: 444
<212> TYPE: DNA
<213> ORGANISM: Artificial Sequence
<220> FEATURE:
<223> OTHER INFORMATION: Optimized rat IL-4

<400> SEQUENCE: 13

```
atgggtttaa gcccccacct tgccgtcaca ctgttctgtt ttctcatctg taccgggaac    60
ggaattcatg gctgtaacga cagccctctg agagagatta tcaacacctt gaatcaggtt    120
accgaaaaag gcactccatg caccgagatg tttgtaccag atgtgcttac ggcaacgagg    180
aacaccactg agaatgagct gatcgtcggg gcttctcgag tgctgcgcaa attctacttc    240
cctcgtgatg tgccccgtg cttgaagaac aagtcaggcg tgctcggaga actgaggaag    300
ctctgcagag gcgtctcagg gctgaattct ctgcgcagct gcaccgtgaa tgaatccaca    360
ctcacaaccc tgaaagactt cctggagagc ctgaagagca tcctacgggg gaagtatctc    420
cagtcctgca cttccatgag ttga                                            444
```

<210> SEQ ID NO 14
<211> LENGTH: 153
<212> TYPE: PRT
<213> ORGANISM: Homo sapiens

<400> SEQUENCE: 14

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 15
<211> LENGTH: 642
<212> TYPE: DNA

<213> ORGANISM: Homo sapiens

<400> SEQUENCE: 15

```
tgcatcgtta gcttctcctg ataaactaat tgcctcacat tgtcactgca aatcgacacc      60
tattaatggg tctcacctcc caactgcttc ccctctgtt cttcctgcta gcatgtgccg      120
gcaactttgt ccacggacac aagtgcgata tcaccttaca ggagatcatc aaaactttga      180
acagcctcac agagcagaag actctgtgca ccgagttgac cgtaacagac atctttgctg      240
cctccaagaa cacaactgag aaggaaacct tctgcagggc tgcgactgtg ctccggcagt      300
tctacagcca ccatgagaag gacactcgct gcctgggtgc gactgcacag cagttccaca      360
ggcacaagca gctgatccga ttcctgaaac ggctcgacag gaacctctgg ggcctggcgg      420
gcttgaattc ctgtcctgtg aaggaagcca accagagtac gttggaaaac ttcttggaaa      480
ggctaaagac gatcatgaga gagaaatatt caaagtgttc gagctgaata ttttaattta      540 tgagttttg atagctttat tttaagta tttatatatt tataactcat cataaaataa         600
agtatatata gaatctaaaa aaaaaaaaa aaaaaaaaa aa                            642
```

<210> SEQ ID NO 16
<211> LENGTH: 28
<212> TYPE: DNA
<213> ORGANISM: Artificial Sequence
<220> FEATURE:
<223> OTHER INFORMATION: Forward primer for amplifying CMV promoter

<400> SEQUENCE: 16

```
ttcggccgtc gaggagcttg gcccattg                                          28
```

<210> SEQ ID NO 17
<211> LENGTH: 36
<212> TYPE: DNA
<213> ORGANISM: Artificial Sequence
<220> FEATURE:
<223> OTHER INFORMATION: Reverse primer for amplifying CMV promoter

<400> SEQUENCE: 17

```
gacgtcgacc tagctagcga attcggggcc gcggag                                 36
```

<210> SEQ ID NO 18
<211> LENGTH: 34
<212> TYPE: DNA
<213> ORGANISM: Artificial Sequence
<220> FEATURE:
<223> OTHER INFORMATION: Forward primer for amplifying SV40pA

<400> SEQUENCE: 18

```
ccatcgatca gacatgataa gatacattga tgag                                   34
```

<210> SEQ ID NO 19
<211> LENGTH: 43
<212> TYPE: DNA
<213> ORGANISM: Artificial Sequence
<220> FEATURE:
<223> OTHER INFORMATION: Reverse primer for amplifying SV40pA

<400> SEQUENCE: 19

```
gacgtcgacg cggccgctac cacatttgta gaggttttac ttg                         43
```

<210> SEQ ID NO 20
<211> LENGTH: 28
<212> TYPE: DNA
<213> ORGANISM: Artificial Sequence

```
<220> FEATURE:
<223> OTHER INFORMATION: Forward primer for amplifying Kanamycin
      resistant gene

<400> SEQUENCE: 20
aggcgccatg agccatattc aacgggaa                                         28

<210> SEQ ID NO 21
<211> LENGTH: 29
<212> TYPE: DNA
<213> ORGANISM: Artificial Sequence
<220> FEATURE:
<223> OTHER INFORMATION: Reverse primer for amplifying Kanamycin
      resistant gene

<400> SEQUENCE: 21
ttcatgatta gaaaaactca tcgagcatc                                        29

<210> SEQ ID NO 22
<211> LENGTH: 28
<212> TYPE: DNA
<213> ORGANISM: Artificial Sequence
<220> FEATURE:
<223> OTHER INFORMATION: Forward primer for amplifying LITR and CMV

<400> SEQUENCE: 22
atggcgcgcc cctggccttt tgctggcc                                         28

<210> SEQ ID NO 23
<211> LENGTH: 28
<212> TYPE: DNA
<213> ORGANISM: Artificial Sequence
<220> FEATURE:
<223> OTHER INFORMATION: Reverse primer for amplifying SV40pA and RITR

<400> SEQUENCE: 23
atggatccgc tagtaaatac cgcatcag                                         28

<210> SEQ ID NO 24
<211> LENGTH: 20
<212> TYPE: DNA
<213> ORGANISM: Artificial Sequence
<220> FEATURE:
<223> OTHER INFORMATION: Forward primer for amplifying rIL-10

<400> SEQUENCE: 24
ccgctagcgc caccatgcct                                                  20

<210> SEQ ID NO 25
<211> LENGTH: 39
<212> TYPE: DNA
<213> ORGANISM: Artificial Sequence
<220> FEATURE:
<223> OTHER INFORMATION: Reverse primer for amplifying rIL-10

<400> SEQUENCE: 25
gacgtcgacg ccatcgatgg cttaattaat caattcttc                             39
```